United States Patent [19]

Cohen et al.

[11] Patent Number: 5,428,078
[45] Date of Patent: Jun. 27, 1995

[54] PROCESS FOR PREPARING ANTIMICROBIAL POLYMERIC MATERIALS USING IRRADIATION

[75] Inventors: Jeffrey D. Cohen, Hockessin, Del.; Carl W. Erkenbrecher, Jr., Elkton, Md.; Sharon Haynie, Philadelphia; Michael J. Kelley, Chadds Ford, both of Pa.; Henry Kobsa, Greenville, Del.; Arthur N. Roe, Houston, Tex.; Michael H. Scholla, Wilmington, Del.

[73] Assignee: E. I. Du Pont de Nemours and Company, Wilmington, Del.

[21] Appl. No.: 320,101
[22] PCT Filed: Nov. 5, 1990
[86] PCT No.: PCT/US90/06473
§ 371 Date: May 4, 1992
§ 102(e) Date: May 4, 1992
[87] PCT Pub. No.: WO91/06593
PCT Pub. Date: May 16, 1991

Related U.S. Application Data

[63] Continuation of Ser. No. 849,375, May 4, 1992, abandoned, which is a continuation-in-part of Ser. No. 431,583, Nov. 3, 1989, abandoned.

[51] Int. Cl.$^6$ .......................... A61K 31/74; C08J 3/28
[52] U.S. Cl. .......................... 522/2; 522/111; 522/164; 522/162; 424/78.32; 424/78.35
[58] Field of Search .......................... 424/78.32, 78.35; 522/164, 173, 174, 149, 111, 2, 162

[56] References Cited

U.S. PATENT DOCUMENTS

| 4,291,142 | 9/1981 | Tamura et al. | 522/164 |
| 4,708,870 | 11/1987 | Pardini | 424/78.35 |
| 4,810,567 | 3/1989 | Calcaterra et al. | 424/78 |

FOREIGN PATENT DOCUMENTS

| 1078457 | 9/1967 | United Kingdom . |
| WO03021 | 5/1987 | WIPO . |

Primary Examiner—Susan W. Berman

[57] ABSTRACT

Polyamide, polyurea, polyhydrazide, and polyurethane materials having substantially modified surfaces which are antimicrobial are disclosed. The disclosure also relates to selective ultraviolet (UV) photon irradiation, high energy electron irradiation low energy electron irradiation for preparing such antimicrobial, polymeric materials. The disclosure further provides methods for controlling microorganisms, and products made from the antimicrobial, polymeric materials of this invention.

6 Claims, No Drawings

PROCESS FOR PREPARING ANTIMICROBIAL POLYMERIC MATERIALS USING IRRADIATION

This a continuation Ser. No. 07/849,375filed May 4, 1992, now abandoned which is a continuation-in-part application of application Ser. No. 07/431,583, filed Nov. 3, 1989, now abandoned.

BACKGROUND OF THE INVENTION

1. Field of the Invention

The present invention relates to certain polymeric materials having substantially modified surfaces which are inherently antimicrobial. The invention also relates to selective irradiation and chemical reducing processes for preparing the antimicrobial materials of the invention, methods of using such antimicrobial materials to control microorganisms, and products and devices comprising such antimicrobial materials.

2. Description of the Prior Art

Although there is no disclosure of imparting antimicrobial properties, laser irradiation of fibers, yarns, and nonwoven materials is known. PCT. Application WO 87/03021, published May 5, 1987, discloses the irradiation of such materials to form depressions and elevations on the surface which improves the material's adhesiveness, frictional resistance and absorptive capacity.

Polyamide materials can also be irradiated with electron energy or treated chemically for grafting purposes, or for improving certain mechanical properties. United Kingdom Patent, 1,078,457, discloses treating polyamide materials with stabilizers such as sodium and potassium borohydride for protecting the materials from discoloration and loss of mechanical strength when exposed to heat or light. Nablo, U.S. Pat. No. 3,774,706, discloses a process of using substantially monochromatic, short-period, high intensity electron beams at a dosage rate considerably in excess of $10^7$ rads/second to bulk-sterilize a wide range of substances. Nablo, U.S. Pat. No. 4,211,622, discloses using electron energy to graft phosphorous or halogen-rich double bonded molecules into materials such as nylon in order to impart flame retardant properties. Tamura et al., U.S. Pat. No. 4,291,142, discloses crosslinked aromatic polyamide films which may be crosslinked by means of heat, ultraviolet (UV) rays, or electron beams. The crosslinked film shows an increased resistance to thermal decomposition. Calcaterra et al., U.S. Pat. No. 4,810,567, discloses a class of antimicrobial fabrics having one or more antimicrobial agents covalently bonded to a graft copolymer of the fabric. The graft copolymer may be formed by electron beam irradiation of a fabric impregnated with a vinyl monomer.

It is also known that antimicrobial properties can be imparted to certain types of acrylic polymers, fibers and fabrics. Pardini, U.S. Pat. No. 4,708,870, discloses an antimicrobial composition of a) at least 85% by weight acrylonitrile, b) up to about 13% by weight of a neutral ethylenically unsaturated monomer, and c) from-about 0.1 to 10% by weight of a protonated amine containing compound. The composition is formed by copolymerization of the acrylic protonated amine comonomer and/or by use of protonated amine end groups.

In accordance with the present invention, it has now been discovered that certain polymeric materials having substantially modified surfaces are antimicrobial. It has also been discovered that selective ultraviolet (UV) photon irradiation, electron irradiation, or chemical reducing agents can impart this property to the polymeric material.

SUMMARY OF THE INVENTION

The present invention relates to certain polymeric materials having substantially modified surfaces which are inherently antimicrobial. These antimicrobial materials include natural and synthetic polyamides, polyureas, polyhydrazides, polyurethanes and copolymers and blends thereof. Each of these materials has a surface containing a sufficient amount of corresponding functional groups, amines and/or hydrazines, to impart antimicrobial activity to the surface.

The antimicrobial, polymeric materials of this invention may be formed by the following methods:
1) ultraviolet (UV) photon irradiation,
2) high energy electron irradiation,
3) low energy electron irradiation, and
4) chemical reduction.

This invention also relates to such irradiation and chemical reduction processes for forming antimicrobial, polymeric materials. Preferably, the UV photons have a wavelength of no greater than 222 nm with an energy density of at least 300 mJ/cm$^2$. Sources of suitable UV photon irradiation include lasers and UV lamps. For electron irradiation, electrons having a kinetic energy of at least 6 eV, at an energy absorption from the electrons of at least 10,000 erg/cm$^3$ of irradiated volume may be used. Preferably, the electrons have a kinetic energy between 100 to 5000 eV, at an energy absorption from the electrons of 50,000 to 250,000 erg/cm$^3$ of irradiated volume. For chemical reduction, the material is treated with an effective reducing agent to form the corresponding functional groups on the surface of the material.

This invention further relates to methods for controlling microorganisms using the antimicrobial materials of this invention, and to products comprising the antimicrobial materials of this invention.

DETAILED DESCRIPTION OF THE INVENTION

This invention relates to processes involving selective UV photon irradiation, electron irradiation, or chemical reducing agents to prepare a polymeric material having a substantially modified surface that is inherently antimicrobial. By the term "inherently antimicrobial" it is meant that the addition of adventitious materials such as biocides, disinfectants, etc., is not necessary for the polymeric material to demonstrate antimicrobial activity.

The term "antimicrobial" as used herein, refers to the reduction of a Klebsiella pneumoniae microbial population by at least 99% in number after 24 hours exposure to the irradiated material produced by the processes of this invention using the Shake Flask Test described, infra.

In accordance with this invention, it has now been found that certain polymeric materials having substantially modified surfaces are antimicrobial. The polymeric materials may be in such forms as, for example, films, fibers, fibrids, powders, or articles made therefrom.

One method for forming such materials involves the excision of carbonyl groups (C=O) from the surface of a material comprising an organic polymer having repeating units of the structural formula,

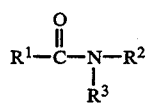

wherein, the polymer is selected from the group consisting of a synthetic or natural polyamide, poly-urea, polyhydrazide, and polyurethane. This excision method may be performed by irradiation and involves excising enough carbonyl groups to form a sufficient amount of a new polymer species which imparts antimicrobial activity to the surface of the material.

Where the polymer is a synthetic polyamide, ($R^1$ is either an alkyl group or an aryl group, $R^2$ is either an alkyl group or an aryl group, and $R^3$ is either hydrogen, an alkyl group, or an aryl group), or a natural polyamide, ($R^1$ is $R_4$—CH(NH), $R^2$ is an alkyl group, and $R^3$ is hydrogen), excision of the carbonyl groups forms a surface Containing a sufficient amount of amine groups to impart antimicrobial activity. For the synthetic polyamide, $R^3$ is preferably hydrogen, because the hydrogen bonding provides the polymer with higher thermal stability and mechanical properties.

Where the polymer is a polyurea, ($R^1$ is NH, $R^2$ is either an alkyl group or an aryl group, and $R^3$ is hydrogen), excision of the carbonyl groups forms a surface containing a sufficient amount of amine and hydrazine groups to impart antimicrobial activity.

Where the polymer is a polyhydrazide ($R^1$ is either an alkyl group or an aryl group, $R^2$ is NHC=O, and $R^3$ is hydrogen), excision of the carbonyl groups forms a surface containing a sufficient amount of hydrazine groups to impart antimicrobial activity.

Where the polymer is a polyurethane, ($R^1$ is oxygen, $R^2$ is either an alkyl group or an aryl group, and $R^3$ is hydrogen), excision of the carbonyl groups forms a surface containing a sufficient amount of amine groups to impart antimicrobial activity.

Alternatively, the polymeric materials may be comprised of a polymer having the functional groups pendant to the polymer chain, rather than in the polymer backbone. The polymeric materials may also be comprised of copolymers and polymer blends of the above described polymers.

The resulting polymer species are not equally distributed throughout the materials. Rather, selective irradiation of the material causes excision of the carbonyl groups and the formation of the new polymer species substantially on the material's surface. By the term "material's surface" it is meant the surface of the material and a depth extending below the surface of less than about 1 micrometer (1 μm). A sufficient number of carbonyl groups are excised to impart antimicrobial activity to the surface of the material. This change in surface chemistry allows the material to inhibit microbial activity, whenever its surface comes into sufficient contact with microorganisms. A sufficient amount of carbonyl groups may be excised by selective UV photon, high energy electron, or low energy electron irradiation.

In a separate method, the surface of materials comprising an organic polymer having repeating units of the structural formula,

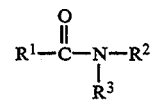

wherein, the polymer is selected from the group consisting of a synthetic or natural polyamide, polyurea, polyhydrazide, and polyurethane may be rendered antimicrobial via chemical reduction.

Where the polymer is a synthetic polyamide, ($R^1$ is either an alkyl group or an aryl group, $R^2$ is either an alkyl group or an aryl group, and $R^3$ is either hydrogen, an alkyl group or an aryl group), or a natural polyamide, ($R^1$ is $R_4$—CH(NH), $R^2$ is an alkyl group, and $R^3$ is hydrogen, an alkyl group, or an aryl group), chemical reduction forms a surface containing a sufficient amount of amine groups to impart antimicrobial activity. For the synthetic polyamide, $R^3$ is preferably hydrogen, because the hydrogen bonding provides the polymer with higher thermal stability and mechanical properties. Where the polymer is a polyurea, ($R^1$ is NH, $R^3$ is either an alkyl group or an aryl group, and $R^3$ is hydrogen), chemical reduction forms a surface containing a sufficient amount of amine groups to impart antimicrobial activity.

Where the polymer is a polyhydrazide ($R^1$ is either an alkyl group or an aryl group, $R^2$ is NHC=O, and $R^3$ is hydrogen), chemical reduction forms a surface containing a sufficient amount of hydrazine groups to impart antimicrobial activity.

Where the polymer is a polyurethane, ($R^1$ is oxygen, $R^2$ is either an alkyl group or an aryl group, and $R^3$ is hydrogen), chemical reduction forms a surface containing a sufficient amount of amine groups to impart antimicrobial activity.

Alternatively, the polymeric material may be comprised of a polymer having the functional groups pendant to the polymer chain rather than in the polymer backbone. The polymeric materials may also be comprised of copolymers and polymer blends of the above-described polymers.

Effective reducing agents for chemically reducing the polymer to its corresponding functional groups are known. Such agents are discussed in Jerry March, *Advanced Organic Chemistry. Reaction Mechanisms, and Structure* (New York: John Wiley and Sons, 1985) and Ian T. Harrison and Shuyen Harrison, *Compendium of Organic Synthetic Methods* (New York: Wiley-Interscience, 1971).

Polyamides, for example, may be rendered antimicrobial by chemical reduction using a variety of reducing agents which are known to reduce amides to their corresponding amines in solution. These include, for example, sodium borohydride in the presence of certain Lewis acids such as aluminum chloride, cobalt (II) chloride ($CoCl_2$), or triethyloxonium fluoroborate, lithium aluminum hydride ($LiAlH_4$), borane, and trichlorosilane. These reagents may be used to reduce the amide groups located substantially on the surface of a polyamide material to amine groups according to the reaction:

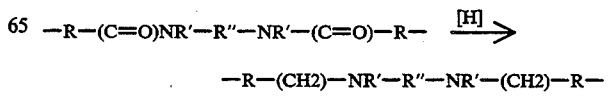

wherein,

R is H, an alkyl group, or an aryl group,
R' is H or an alkyl group, and
R" is an alkyl group or an aryl group.

While the resulting product is not identical to that species formed by excision of the carbonyl groups, the final result is the formation of a secondary or tertiary amine which renders the material's surface antimicrobial. If the amide groups are pendant to the polymer chain, rather than in the polymer backbone, a primary amine may also be formed depending upon the degree of nitrogen substitution.

Reaction conditions should be chosen such that reduction occurs only at the functional groups located at or near the surface of the polymeric material. For example, treatment of polyamide fibers using lithium aluminum hydride in refluxing tetrahydrofuran (THF) was found to result in significant loss in fiber weight. This may be due to excessive reduction of the amides over substantially the entire length of the polymer molecules resulting in soluble polyamine species. When the reaction is carried out at room temperature, loss of fiber mass is not observed.

The new polymer species formed by the above-described methods are chemically bound to the surface via the sub-surface portions of the polymeric chains which have not been transformed by irradiation or reduction. Thus, the new polymer species do not leach into solutions which are contacted with the treated materials.

Suitable polymers for irradiation or reduction include, for example, synthetic polyamides such as poly(hexamethylene adipamide), poly(ε-caproamide), and poly(metaphenylene isophthalamide); natural polyamides such as wool, silk, and casein: polyureas, polyhydrazides, and polyurethanes.

The chemically reduced or irradiated material forms a new polymer species substantially on its surface which becomes progressively more protonated over a range of a pH of about 9 to a pH of about 5. At a pH of about 7, the polymer species are largely protonated, and at a pH of about 5, they are effectively all protonated. At a pH much above 9, the new polymer species are not protonated, and thus are not effective as antimicrobial agents.

It has been found that in order to achieve the desired antimicrobial activity by irradiation, the polymeric material must be in a form having a specific surface area such that at least 0.02 m²/g and preferably at least 0.20 m²/g of the material's surface area can be irradiated. "Specific surface area" as used herein, can be determined by standard gas absorption techniques or, in the case of filamentary materials, by the following formula:

$$\text{Specific Surface Area (m}^2\text{/g)} = \text{the square root of } \frac{0.004 \times \pi}{\rho \times \text{Tex}}$$

wherein,
p is the density of the polymer(g/cm³) and Tex is the linear density of the individual filaments(g/1000 m).

"Specific irradiated surface area" as used herein, refers to the specific surface area times the fraction irradiated. It is the irradiated specific surface area of a unit quantity of material. The fraction of the surface area irradiated for drawn fibers and stretched films is determined by examining the surface of the material with a scanning electron microscope. Drawn fibers and stretched films, when irradiated, exhibit characteristic features on the surface of the material such as transverse ridges as described in PCT application WO 87/03021. The fraction of the specific surface area irradiated is computed by dividing the fraction containing these ridges by the total surface area. Undrawn yarns and unstretched films, when irradiated are smooth and the specific irradiated surface area is inferred from the manner in which the material was irradiated. The specific irradiated surface area of the material approaches the specific surface area of the material when the form of the material is a card web or spunlaced fabric, a very open structure of low basis weight, and is a much smaller fraction, for example when the material is a fabric formed of a twisted yarn.

When the specific irradiated surface area of the material is less than 0.20 m²/g, such as in most yarns, a relatively high level of energy must be imparted to the material to achieve the antimicrobial properties of the invention.

The materials used in the processes of this invention can be, for example, in the shape of films, fibers, fibrids, powders, or articles made therefrom. A particularly preferred article is a spunlaced fabric produced in accordance with the general procedures of Evans, U.S. Pat. No. 3,485,706, which is hereby incorporated by reference. Spunlaced fabrics generally have a suitable specific surface area for practicing the processes of this invention and are in a convenient form to be irradiated to the required fraction of the specific surface area. When the article is to be irradiated, woven and knit fabrics are less preferred, since high overlap among the fibers causes large portions of the article's surface to be shaded from the irradiation. For such an article, chemical reduction would be more effective.

In the present invention, one method for imparting antimicrobial activity to the material by irradiation is through ultraviolet (UV) photons. The term "UV photons", as used herein, refers to photons having a wavelength from 400 to 10 nm. Any source of photons can be employed that generates light with the power and energy as described herein, and that emits a wavelength that the article is capable of strongly absorbing as defined herein. Preferably, the UV photon wavelength is no greater than 222 nm, and more preferably the wavelength is no greater than 193 nm. Suitable UV photon sources include, for example, Excimer lasers and ultraviolet (UV) lamps. Preferably, an ArF Excimer laser which generate wavelengths of 193 nm is used. ArCl lamps which generates wavelengths of 222 nm, ArF lamps which generate wavelengths of 193, and Xe lamps which generate wavelengths of 172 nm may also be used. The photon source, particularly the UV lamp, is best operated in a non-absorbing, non-reactive gas or vacuum environment, e.g., not air.

It has been found that the material must be capable of strongly absorbing UV photon radiation. The phrase "the material must be capable of strongly absorbing" as used herein, is meant to include materials that directly absorb the UV photon energy.

Materials that strongly absorb UV photon radiation will generally absorb at least about 50% of the photon energy in about the first 20% of the thickness of the material or depending on the form, often about the first micrometer (1 μm) of the surface of the article being irradiated. The absorptivity at the wavelength of the UV photon radiation is measured in a spectrophotometer using a film of the material at a known thickness.

The reduction in light intensity (I) from $I_o$ to I is determined by the following equation;

$$I = I_o * 10^{-\alpha * d}$$

wherein, d is the distance into the material.

Therefore, in order for at least 50% of the energy to be absorbed in the first 20% of the thickness of the material, $\alpha$ must be at least 1.5/D where D is the thickness of the material ($\alpha*d$ must be at least 0.3 when d is 0.2,*D). Examples of strongly absorbing materials as defined herein, include a 1 denier per filament (dpf) (0.111 Tax) fiber with a diameter (thickness) of 11 micrometers having an $\alpha$ of at least 0.14 reciprocal micrometers ($\mu m^{-1}$). A 1 mil film having a thickness of 25 micrometers strongly absorbs UV photons when $\alpha$ is at least 0.06 $\mu m^{-1}$. A 20 dpf (2.22 Tax) fiber having a thickness of 50 micrometers strongly absorbs UV photons when $\alpha$ is at least 0.03 $\mu m^{-1}$. However, a higher absorbance of about 0.3 ($\mu m^{-1}$) is preferred. Specifically, poly(hexamethylene adipamide) fibers irradiated by photons having a wavelength of 193 nm, strongly absorb photons with an $\alpha$ of 0.86 $\mu m^1$. When the photon wavelength is 248 nm, poly(hexamethylene adipamide) weakly absorbs photons with an $\alpha$ of 0.0096 $\mu m^{-1}$.

The material to be used in the present invention must be irradiated with a UV photon energy density of at least 300 mJ/cm$^2$. Energy densities below 300 mJ/cm$^2$ either produce no antimicrobial activity or do not produce useful levels of antimicrobial activity. When the specific surface area of the material is less than 0.2 m$^2$/g, an energy density of at least about 1.0 J/cm$^2$ should be employed. Further, it has been found that when the material is at least partially aromatic or wholly aromatic such as poly(metaphenylene isophthalamide), a UV photon energy density of at least about 3 J/cm$^2$ should be employed to yield useful levels of antimicrobial activity. Upper limits on photon energy are governed by a desire to reasonably maintain the material's structural integrity.

If an Excimer laser is used, the UV photon energy is generally imparted to the material at an irradiance of about 200 kw/cm$^2$, and more typically at 4 MW/cm$^2$ for 16 nanoseconds in order to achieve the antimicrobial activity of this invention. If an ultraviolet (UV) lamp is used, the UV photon energy is generally imparted to the material at an irradiance of about 1 W/cm$^2$ for 3,500 seconds.

Alternatively, electron irradiation may be used to impart antimicrobial activity to the material. In electron irradiation, a flux of electrons impinges on materials passing through an electron beam.

The extent to which the electrons impart antimicrobial activity to the material is a function of the number of electrons delivered per unit of specific surface area (dosage), and the probability that each electron will cause the desired effect (cross-section). The cross-section increases as the kinetic energy of the individual electrons decreases, until the energy falls below a critical minimum of about 6 electron volts (eV). As a result, the required dosage of high energy electrons is much higher than the dosage needed for low energy electrons.

Furthermore, the depth of electron penetration is a function of the initial kinetic energy of the electrons, i.e., electrons having lower energy have less penetration, and the composition of the material, i.e., electrons more easily penetrate materials having a low average atomic number, such as organics. For organic materials, as described in C. A. Andersen and M. F. Hasler, "Extension of Electron Microprobe Techniques," *4th International Congress of X-ray Optics and Microanalysis,* eds. R. Castaing, P. Deschamps, and J. Philibert (Paris: Hermann, 1966), pp. 310-327, the penetration of electrons having an initial kinetic energy up to at least 50,000 eV increases approximately as the 1.68 power of energy. This relationship is defined in the following formula, $$Dp = \frac{0.064 \, (E)^{1.68}}{p}$$

wherein,

Dp is the penetration depth in micrometers, (E) is the electron kinetic energy in thousands of electron volts (ev), and p is the density in grams per cubic centimeter (g/cm$^3$).

The term "irradiated volume" as used herein, is the product of the irradiated specific surface area by the penetration depth.

In the present invention, it is desirable to deposit the energy of the electrons on the surface of the material in order that any chemical changes may occur substantially on the surface, and thus maintain the material's structural integrity. As more electrons penetrate the material, the likelihood of structural damage increases.

It is appreciated that this radiation-induced chemical reaction will proceed to the depth of electron energy penetration. However, for the present invention, it is important that the new polymer species forms substantially on the surface of the material to impart useful antimicrobial activity. Therefore, the depth of electron energy penetration is preferably less than about one micrometer (1 m). For a thick section of a highly porous material, a sufficiently high electron energy which penetrates the entire thickness is preferred.

In the present invention, an electron energy of at least 6.4 eV at an energy absorption from the electrons of at least 10,000 erg/cm$^3$ of irradiated volume is required to impart antimicrobial activity to the surface of the material. Preferably, the electron energy is no greater than 10,000,000 eV and the energy absorbed from the electrons is no greater than 1,000,000 erg/cm$^3$ of irradiated volume. More preferably, the electron energy is from 100 to 5000 eV, and the energy absorbed from the electrons is from 50,000 to 250,000 erg/cm$^3$ of irradiated volume.

The present invention also provides processes for controlling microorganisms using the antimicrobial materials of the invention. Microorganisms can be controlled in a variety of media by contacting an effective amount of the antimicrobial material with a microorganism. A convenient medium is an aqueous medium and a gaseous medium would behave similarly. Contacting the skin or other parts of a mammal with an effective amount of the antimicrobial material would also be expected to control microorganisms.

The antimicrobial material of the present invention controls a broad spectrum of microorganisms. The material has been found to be useful in controlling bacteria, myceteae and viruses using the Shake Flask Test described, infra. The antimicrobial material would also be expected to control algae, protozoa, viroids and prions in a similar manner.

By the term "bacteria" is meant eubacteria and archaebacteria. Eubacteria include fermicutes, gracilicutes and ternicutes. Gracilicutes include gram-negative, facultatively anaerobic rods. Gram-negative, facultatively anaerobic rods include Enterobacteriaceae. Enterobacteriaceae include Klebsiella and Escherichia. Klebsiella include *Klebsiella pneumniae* and Escherichia include *Escherichia coli*. Fermicutes include the group gram-positive cocci, and the group endospore-forming rods and cocci. Gram-positive cocci include Micrococcaceae. Micrococcaceae include Staphylococcus and Staphylococcus includes *Staphylococcus aureus*. Endospore-forming rods and cocci include Bacillaceae. Bacillaceae includes Bacillus which includes *Bacillus circulans*. All references herein to bacteria are in accordance with *Bergey's Manual of Systematic Bacteriology*, Williams & Wilkens, 1st ed. Vol. 1–4, (1984).

The term "Myceteae" includes Amastigomycota. Amastigomycota include Deuteromycotina which includes Deuteromycetes. Deuteromycetes include Aspergillis and Candida. Aspergillis includes *Aspergillis niger* and Candida includes *Candida albicans*.

The term "virus" includes bacteriophage. Bacteriophage includes T-series bacteriophage which includes T-even bacteriophage such as bacteriophage T4.

Examples of suitable applications comprising the antimicrobial articles and materials of the present invention include medical applications, dental devices, food wrap, floor coverings such as carpet backings, and coatings. More specifically, examples of medical devices include wound closure devices, such as those sutures which are generally described in "Gore-Tex" Suture Bulletins, W. L. Gore & Assoc., Inc. (1986). Examples of devices for purifying or sterilizing aqueous solutions include those which are generally described in *Gelman Sciences Process Microfiltration Catalog*, (April 1986). Similarly, examples of devices for purifying or sterilizing a gas include those which are generally described in "Nonwovens in Filtration (1987) Worldwide," *Filter Media Consulting. Inc.*, (April 1988). Examples of catheters include those generally described in "MEDSPEC 1989," *Medical Devices Register, Inc.*, (1989). Examples of suitable devices for storing, transporting or dispensing sterile solutions, devices for controlling odors, wound dressings and garments such as gowns and masks are generally described in "Hospital Supply Index," *Product Analysis*, Vol. 1A and 1D, IMS America Ltd., (Third Quarter 1986). Examples of medical implants are generally described in "The Orthopedic Implants and Allied Products Markets Outside the U.S.," *Frost & Sullivan, Inc.*, (April 1985). Examples of floor coverings, such as carpet backing, are generally described in Edwards, U.S. Pat. Nos. 3,563,838, Hendersen, 3,821,062 and Peterson, 3,502,538. Examples of food wraps are generally described in *Chemical week*, Mar. 13, 1983, p. 11. Examples of coatings are generally described in *Biomedical Business International*, Mar. 2, 1988, pp. 37–38 (Medical), *Textil Praxis International*, foreign edition with English supplement, 1980, vol 35, pp. XVI–XXIII (Consumer), and *West Marine Products Catalog*, (P.O. Box 1020 Watsonville, Calif. 95077) (Summer 1989) pp. 99–100 (Marine). Examples of tests in which a preservative comprising the antimicrobial material of the present invention could be used are described in "United States Pharmacopeia, Microbiological Tests (51)," *Antimicrobial Preservative Effectiveness*, Vol XXII pp. 1478–1479 (1990).

Testing Methods

Antimicrobial activity was measured using the Shake Flask Test described generally in U.S. Pat. No. 4,708,870 and outlined in Malek and Speier, *The Journal of coated Fabrics*, vol. 12, July 1982, pp. 38–45.

The Shake Flask Test requires the test material to be in a form having a high surface area to weight ratio. Furthermore, the surface area should be predominantly treated so as to detect antimicrobial activity. Articles having the form of powders, fibers, and thin films have proven to be acceptable. For instance, treating the surface of a polymer cube weighing 0.75 g and then milling this into a powder prior to the Shake Flask Test may not provide the necessary treated surface area to detect antimicrobial activity. However, treating the milled powder would be acceptable.

The bacterial inoculum for the Shake Flask Test was prepared by transferring 2.0 ml of an overnight broth culture to a 300 ml nephyloculture flask (Bellco Glass Inc., Vineland, N.J.) containing 100 ml of Tryptic Soy Broth (TSB) (Remel, Lexena, Kans.). This flask was incubated at 373C with shaking (ca. 200 rpm). Growth of the culture was determined during incubation using a Klett-Summerson photoelectric colorimeter (Klett Mfg. Co., NY, N.Y.). When the culture reached late-log phase (185–200 Klett units for *Klebsiella pneumonias* ATCC 4352), appropriate dilutions were made with sterile 0.2 mM phosphate buffer (pH 7).

This inoculum was then placed into sterile, disposable 250 ml Erlenmeyer flasks (Corning Glass Co., Corning, N.Y.) containing 0.75 g of the Material produced by the process of this invention or a suitable control material as indicated below. Each flask contained a known concentration of bacteria in a final volume of 75 ml phosphate buffer.

The initial concentration of bacteria used in the various examples was determined by serial dilution of the inoculum (0.2 mM Phosphate buffer, pH 7) and plating in triplicate on Trypticase Soy Agar (TSA) plates (sold commercially by BBL, Cockeysville, Md.). The flasks were shaken on a Burrell wrist action shaker (Burrell Corp., Pittsburgh, Pa.). A 1.2 ml aliquot was removed from each flask after shaking for 1 hour (or other appropriate time interval as indicated). Duplicate petri plates containing TSA were inoculated via spread plating with 0.1 ml each of the sample. The remaining 1.0 ml was serial diluted and plated in duplicate. The TSA plates were incubated at 373C. for 18 to 24 hours. Plates having between 30 and 300 colonies were counted and the bacterial concentration determined from the mean of the plate counts. If none of the plates contained at least 30 colonies, all colonies were counted and the bacterial concentration determined from the mean of the plate counts. Below the limit of detection of the procedure described herein, the colony count was said to be zero.

Alternately, microbial enumeration was performed using impedance techniques via a Bactometer Model 123 Microbial Monitoring System. Two Bactometer wells containing Double Strength Plate Count Agar were inoculated with 0.1 ml of sample from each flask. The modules were incubated at 353C. and the impedence monitored. Densities of *K. pneumoniae* were calculated based upon comparing the sample impedance detection time to an impedence vs. cfu/ml (colony forming units per milliliter) standard curve. Detailed description of this methodology is found in R. Firstenberg-Eden, R. and G. Eden, *Impedance Microbiology*, (Letchworth, Hertfordshire, England: Research Studies Press Ltd., 1984), pp. 170.

When the Shake Flask test was conducted using Bacteriophage T4 for examples 74 and 75, the titer was determined by plaque assay as described in F. M. Ausubel et al., eds., *Current Protocols in Molecular Biology*, Section 3, Unit 1.11 (New York: John Wiley and Sons, Escherichia coli HB101 was used as the host.

Antimicrobial activity was determined by the formulas:

$$k_t = \log 10(C_o) - \log 10(C_t + 1)$$

$$D_t = \log 10(CF_t) - \log 10(C_t + 1)$$

where:
$C_o$ = initial concentration of bacteria (cfu/ml) in test flask at time zero,
$C_t$ = concentration of bacteria (cfu/ml) in test flask at time t (one is added to the number to avoid calculating the log of zero),
$CF_t$ = concentration of bacteria (cfu/ml) in control flask at time t, and
cfu/ml = colony forming units per milliliter.

The relationship between percent reduction and log reduction is conveniently seen by reference to the following:

| % Reduction | Log Reduction | $K_t$ |
|---|---|---|
| 90 | 1 | 1 |
| 99 | 2 | 2 |
| 99.9 | 3 | 3 |
| 99.99 | 4 | 4 |
| 99.999 | 5 | 5 |

In all the Examples, the organic polymer was tested substantially free of fiber finish. In Examples 1-76, the finish was removed by known techniques such as washing with methanol and carbon tetrachloride either before or after irradiation. In Examples 77 to 115, the finish was removed as described, infra.

Laser irradiation for examples 1 to 76 was performed using Excimer laser models EMG 101MSC, EMG MSC or LPX 325iCC all manufactured by Lambda Physik, Goettingen, Federal Republic of Germany. The laser contained standard mixtures selected from the following gases: argon, fluorine, neon and helium. Light was emitted from the laser at a wavelength of 193 nm and in pulses of about 16 nanoseconds. All irradiation was carried out under ambient conditions.

High energy electron beam irradiation for examples 77 to 107 was performed using an electron beam accelerator, Model KS, available from High Voltage Inc.

Low energy electron beam irradiation for examples 108 to 110 was performed using the following described apparatus.

The apparatus included a metal vacuum vessel having a pumping system capable of reducing pressure to 0.00002 torr (mm of Hg), a gauge for measuring pressure, a door that could be opened to introduce and remove samples, and such additional, conventional features which are known to those skilled in the art. These features are described in texts such as A. Roth, *Vacuum Technology*, 2nd ed. (New York: North-Holland Publishing Co., 1982), or in J. F. O'Hanlon, *A Users Guide to Vacuum Technology*, 2nd ed. (New York: Wiley, 1989).

The apparatus also contained the following internal parts. A rotatable platen which was driven by a motor controlled externally by an operator. The sample material to be treated was attached to the lower surface of the platen by "Kapton" tape and applied only to regions of the sample that would be cut off after the treatment was complete. The platen was electrically connected to the vessel. A filament assembly having three strands of 0.01 inch diameter tungsten wire was connected in parallel between two insulated posts and positioned below the platen. The two posts were insulated from the vacuum vessel and from each other. The distance between the posts was such that the length of the filament assembly was approximately 3 inches. The height of the posts was such that the filament assembly was approximately 1.5 inches above the base. The base was metal and electrically isolated. The platen was approximately 4.75 inches above the filament assembly. The posts to which the tungsten wires were attached were each connected electrically to an individual terminal external to the vacuum vessel. The filament assembly was located off-center with respect to the center of rotation of the platen such that the filament assembly's center was approximately at a horizontal distance of 2.5 inches from the center of the platen. The filament assembly was oriented such that the wires were approximately parallel to the radius of the platen above them. An 1.5 inch diameter circle of stainless steel sheet having no protrusions on its front face, a current probe, was placed in various locations in the vessel and oriented such that the surface normal of the sheet pointed towards the filament assembly. The current probe was electrically isolated, except for being connected electrically to a terminal external to the vacuum vessel.

The electrical connections of the apparatus were as follows. The vacuum vessel was connected to electrical ground. The beam power supply was connected so as to impress an adjustable voltage between the filament assembly and the ground such that the filament assembly was negative with respect to the ground. This voltage between the filament assembly and the ground was the beam voltage. The current drawn from the beam power supply was the beam current. The current probe was connected to the ground through a device to measure the current. This current flowing between the ground and the current probe was the probe current. A power supply which was isolated from the ground was connected such that it could impress a voltage between the two insulated posts that supported the filament assembly. This voltage was the filament power supply. The current drawn from the filament power supply was the filament current and could be adjusted by the operator.

A sheet of the sample material to be treated was attached to the platen and the access to the vacuum vessel interior was closed. Valves to the pumps were opened and pumping continued until the pressure fell below 0.00004 torr. The platen rotation motor controller was set to the speed chosen for the sample, typically 60 rpm. The filament power supply was adjusted to obtain electron emission, typically 0.9 amperes. The beam power supply was adjusted to obtain the beam voltage chosen for the experiment. The beginning of treatment was defined as the instant when the beam current flow began. Treatment continued for the specific time chosen for the sample. Treatment ended when the flow of beam current was stopped. It will be appreciated that the rotation of the platen caused the sample to move above the filament assembly so that a ring of material was thus exposed to the strongest irradiation. As soon as the treatment was stopped, the flow of filament current was stopped and the filament assembly was allowed to cool. Air was then let into the vacuum vessel and the access door was opened. The sample was then turned over such that the side which was previously against the platen now faced outward. Care was taken to ensure that the center of the platen on the sample was at the same location after the sample was turned over. The second side was subsequently treated in the same manner as the first side.

X-Ray Photoelectron Spectroscopy (XPS)

X-ray Photoelectron Spectroscopy (XPS, also known as ESCA) is well established as a means for obtaining elemental and chemical state information from solid surfaces, including polymers. See for example "*Practical Surface Analysis by Auger and X-ray Photoelectron Spectroscopy*", D. Briggs and M. P. Seah, eds., John Wiley & Sons, New York), 1983. Electrons are emitted and escape without energy loss from a depth of not less than a few nanometers below the solid surface. The kinetic energy of these electrons is the difference between the energy of the x-rays which were used to eject and the energy binding them in the orbitals of the atoms from which they came. Since the set of orbital energies is unique to each element, measuring the energy distribution of these emitted electrons provides a means of elemental analysis. Moreover, the orbital energies may shift by a small amount, typically a few electron volts or less, when the atoms are combined into chemical compounds, the "chemical shift".

Thus the x-ray photoelectron spectrum of 6/6 nylon shows electrons at energies corresponding to carbon, nitrogen and oxygen. Looking more closely in the energy range for electrons emitted from the 1s orbital of carbon (C 1s peak), two groups separated by about 3 eV are seen. It is known that the more numerous lower binding energy group corresponds to carbon in aliphatic bonds, while that of the higher energy group corresponds to carbon in a carbonyl environment.

The surface analysis for the Examples was performed using an Escalab-2 surface analysis instrument available from VG Instruments, Inc., Danvers, Mass. The instrument was operated according to the ordinary practice for such instruments as described in the operator's manual supplied by the vendor. For X-Ray Photoelectron Spectroscopy (XPS), the magnesium anode was used with the power supply set to supply a current of 20 milliamperes at 15,000 volts. The electron energy analyzer iris was set to 14, the aperture to 3 mm, and the pass energy to 50 eV. In a few cases, a large enough sample was available to use a 15 mm×6 mm aperture instead of the 3 mm aperture, and thus collect data at a faster rate. Samples were placed into the instrument by attaching them to one of the sample stubs supplied with the instrument. The stubs provided a flat, horizontal surface, about 10 mm in diameter, to which the samples were attached.

To analyze a fabric, a sample, about 1×2 cm was cut from the fabric and washed with fresh, reagent grade trichlorotrifluoroethane, known commonly as "Freon" TF, purchased from Miller-Stephenson Co. Inc. of Danbury Conn. as type MS-182. After washing, the sample was handled only with similarly cleaned tweezers. Two pieces of fabric, each being at least 5×5 mm, but small enough not to extend beyond the perimeter of the stub, were cut from the washed sample of fabric and set one on top of the other on the sample holding stub of the surface analysis instrument. A square of common aluminum foil, about 15×15 mm, was cut and a hole, about 4 mm in diameter, was punched through it, approximately at the center. The aluminum foil was then washed and handled subsequently in the same manner as the fabric sample. The aluminum foil was placed over the fabric pieces on the stub so that the hole in the foil was more or less at the center of the stub and the fabric was visible through it. The edges of the foil were crimped down over the top of the stub in order to hold the fabric pieces in place. The fabric pieces were then put into the surface analysis instrument.

The standard data collection practice consisted of a survey scan extending in binding energy from 25 electron volts to 1125 electron volts in steps of 0.7 eV, counting for 200 milliseconds at each step. The purpose of the survey scan was to detect the presence of any unanticipated contaminants. Spectra were also collected from the neighborhood of the 1s peaks of carbon, oxygen and nitrogen. These spectra went from about 5 eV below the expected peak position to about 10 eV above it, in steps of 0.1 eV. Data was collected. Typically 1000, 8000, and 4000 milliseconds per data point were used for carbon, nitrogen and oxygen, respectively. These times were adjusted to compensate for variations in concentration, or to provide still better data quality when it was needed for more demanding forms of data analysis.

The data was analyzed using the computer programs supplied with the instrument by the vendor in the manner described in the vendor's manuals. Applying these programs to the data from the carbon, nitrogen and oxygen 1s peaks gave the elemental composition of surface in terms of the atom percent of each element. The carbon 1s peak was further analyzed to quantitatively determine the relative amounts of individual contributions, especially carbonyl. The assignments of contributions were made according to accepted values appearing in the scientific literature. The separation of the peak into contributions was accomplished by means of the computer programs supplied by the vendor with the instrument used in the manner set forth in the vendor's manuals.

Four samples of untreated poly(hexamethylene adipamide) fabric: (poly(hexamethylene adipamide) fibers sold commercially by E. I. du Pont de Nemours and Company as type 200SD having a dpf of 1.8 (0.2 Tex) were spunlaced to yield a fabric) were analyzed in the foregoing manner. The results are shown in Table A.

TABLE A

| Test Number | Carbon | Nitrogen | Oxygen | Carbonyl |
|---|---|---|---|---|
| 83 | 79.545 | 9.169 | 11.286 | 13 |
| 85 | 78.535 | 9.928 | 11.537 | 14 |
| 223 | 78.710 | 10.037 | 11.252 | 14 |
| 227 | 79.107 | 10.627 | 10.266 | 14 |

The values for carbon, nitrogen and oxygen are in atom percent. The value for carbonyl is the percent of the total carbon 1s peak that arises from carbon in a carbonyl environment. The agreement between the carbonyl content and the carbon/oxygen ratio indicates that essentially all the oxygen in the polymer is present as the carbonyl.

Four samples of poly(hexamethylene adipamide) fabric: (poly(hexamethylene adipamide) fibers sold commercially by E. I. du Pont de Nemours and Company as type 200SD having a dpf of 1.8 (0.2 Tex) were spunlaced to yield a fabric) irradiated by a laser in a similar manner as described in Table I, Radiation Treatment A4, infra, were also examined. The results are shown in Table B.

TABLE B

| Test No. | Carbon | Nitrogen | Oxygen | Carbonyl |
|---|---|---|---|---|
| 81 | 79.540 | 8.787 | 11.674 | 12 |
| 79 | 80.165 | 8.924 | 10.911 | 10 |
| 103 | 79.100 | 8.675 | 12.224 | 8 |
| 109 | 80.951 | 8.961 | 10.089 | 8 |

From Table B it is seen that about 25% to about 50% of the carbonyl groups have been removed. The values for the carbon, nitrogen, and oxygen are atom percent, and carbonyl is the percent of the total carbon 1s peak that arises from carbon in a carbonyl environment. It is noted that the carbonyl contribution has decreased for the irradiated samples. The significance of this decrease is made clearer by noticing that if half the carbonyl groups were excised, the carbonyl fraction for the irradiated samples would be half the value of the carbonyl fraction for the unirradiated samples, i.e, decreasing from about 14 to about 7. It is also noted that in the irradiated samples, there is more oxygen than can be accounted for by the carbonyl groups, indicating that other oxygen species are present. The differences among the irradiated samples can be attributed to the irradiation procedures which do not assure precisely the same photon dose to each and every location on the fabric surface.

The following designations are referred to in the Examples below:
1. IC; Designates "Inoculated Control" and refers to a flask containing buffer and bacteria alone.
2. UC; Designates "Uninoculated Control" and refers to a flask containing buffer alone.
3. PC; Designates "Positive Control" and refers to poly(ethylene terephthalate) yarn treated with 0.15% by weight of a 72% by weight in methanol solution of the antimicrobial agent 3(trimethoxysilyl) propyloctadecyldimethyl ammonium chloride. The antimicrobial agent is sold commercially by Dow Chemical Co. Midland, Mich. as DC-5772. The yarn treated with DC-5772 is sold commercially by E. I. du Pont de Nemours and Company as type D212 Dacron$^R$ yarn. The yarn has a denier per filament of 28.0 and a specific surface area of 0.054 $m^2$/g.
4. NC; Designates "Negative Control" and refers to poly(ethylene terephthalate) yarn having a denier per filament of 28.0 and a specific surface area of 0.054 $m^2$/g. The yarn is sold commercially by E. I. du Pont de Nemours and Company as type D692 "Dacron" yarn.

LASER IRRADIATED EXAMPLE 8

SPUNLACED FABRIC EXAMPLES

Irradiation Conditions

A variety of organic polymeric materials were spunlaced according to the general procedure of Evans U.S. Pat. No. 3,485,706. The spunlaced fabrics were irradiated by placing 1 $m^2$ samples on a drum roller having a 1 m circumference. Exposure of the sample to the light beam was controlled by rate of drum rotation and lateral movement of the drum. The fabric was turned over to expose the back of the spunlaced fabric to the laser light and the process of irradiation repeated. Greater than 90% of the specific surface area of the spunlaced fabrics were irradiated as determined by scanning electron microscope.

For all spunlaced fabrics, an Excimer laser model EMG 202MSC was operated at 100 Hz with an energy output of 150 mJ/pulse. The beam area for treatment A shown in Table I was 1.76 $cm^2$. The beam area was reduced for radiation treatments B, C, D and E using a $MgF_2$ cylindrical lens with a focal length of 256 mm at a wavelength of 193 nm.

For all spunlaced examples shown in Tables II and III, the drum was rotated at 24 rpm. Lateral speed of the drum passing in front of the laser was varied as shown in Table I to result in 50% circumferential and 50% lateral overlap of beam area, so that any one point on each side of the fabric was exposed to 4 pulses of light in one pass of the drum in front of the beam.

Irradiation conditions for spunlaced fabric examples are detailed in Table I. As an illustration, radiation treatment A1 results in greater than 90% of the specific surface area of the fabric receiving 0.34 J/$cm^2$ in one pass.

TABLE I

Irradiation Conditions for Spunlaced Fabrics

| Radiation Treatment | Lens | Lens Distance (mm) | Lateral speed (cm/min) | Passes | Irradiance (MW/$cm^2$) | Energy/Pulse (mJ/$cm^2$) | Total Energy (J/ |
|---|---|---|---|---|---|---|---|
| A1 | NO | NA | 26.4 | 1 | 5.3 | 85 | 0.3 |
| A2 | NO | NA | 26.4 | 2 | 5.3 | 85 | 0.6 |
| A3 | NO | NA | 26.4 | 4 | 5.3 | 85 | 1.3 |
| A4 | NO | NA | 26.4 | 8 | 5.3 | 85 | 2.7 |
| A5 | NO | NA | 26.4 | 16 | 5.3 | 85 | 5.4 |
| A6 | NO | NA | 26.4 | 32 | 5.3 | 85 | 10.9 |
| B1 | YES | 128 | 13.2 | 1 | 10.6 | 170 | 0.6 |
| B2 | YES | 128 | 13.2 | 2 | 10.6 | 170 | 1.3 |
| B3 | YES | 128 | 13.2 | 4 | 10.6 | 170 | 2.7 |
| B4 | YES | 128 | 13.2 | 8 | 10.6 | 170 | 5.4 |
| B5 | YES | 128 | 13.2 | 16 | 10.6 | 170 | 10.9 |
| C1 | YES | 191 | 6.6 | 1 | 21.0 | 340 | 1.36 |
| C2 | YES | 191 | 6.6 | 2 | 21.0 | 340 | 2.72 |
| C3 | YES | 191 | 6.6 | 4 | 21.0 | 340 | 5.44 |
| C4 | YES | 191 | 6.6 | 8 | 21.0 | 340 | 10.90 |
| D1 | YES | 223 | 3.3 | 1 | 43.0 | 680 | 2.72 |
| D2 | YES | 223 | 3.3 | 2 | 43.0 | 680 | 5.44 |
| D3 | YES | 223 | 3.3 | 4 | 43.0 | 680 | 10.90 |
| E1 | YES | 239 | 1.7 | 1 | 85.0 | 1360 | 5.44 |
| E2 | YES | 239 | 1.7 | 2 | 85.0 | 1360 | 10.9 |

Spunlaced Poly(hexamethylene adipamide) fabric: Poly(hexamethylene adipamide) fibers sold commercially by E. I. du Pont de Nemours and Company as type 200SD having a dpf of 1.8 (0.2 Tex) were spunlaced to yield a fabric with a basis weight of 44 g/m². The spunlaced fabric had a specific surface area of 0.235 m²/g.

Irradiated poly(hexamethylene adipamide) spunlaced fabric demonstrated antimicrobial activity as determined by the Shake Flask Test. In all cases except for Example 2, after 1 hour exposure to irradiated poly(hexamethylene adipamide) fabric, the population of *Klebsiella pneumoniae* was reduced by greater than 99%. Complete reduction was evident in poly(hexamethylene adipamide) spunlaced fabric examples irradiated with as little energy as 1.36 J/cm². By 24 hours, all irradiated poly(hexamethylene adipamide) examples reduced the bacterial population below the limit of detection.

Results are detailed in Table II.

TABLE II

Antimicrobial Activity Associated with Irradiated Spunlaced Poly(hexamethylene adipamide)

| Example | Radiation Treatment | Initial* cfu/ml | 1 Hour cfu/ml | $k_t$ | $D_t$ |
|---|---|---|---|---|---|
| 1 | None | 1.50E+05 | 1.51E+05 | 0.00 | 0.00 |
| 2 | A1 | 1.50E+05 | 1.87E+03 | 1.90 | 1.90 |
| 3 | A2 | 1.50E+05 | 7.50E+00 | 4.30 | 4.30 |
| 4 | A3 | 1.50E+05 | 2.50E+00 | 4.78 | 4.78 |
| 5 | A4 | 1.50E+05 | 0.00E+00 | 5.18 | 5.18 |
| 6 | A5 | 1.50E+05 | 2.50E+00 | 4.78 | 4.78 |
| 7 | A6 | 1.50E+05 | 0.00E+00 | 5.18 | 5.18 |
| 8 | B1 | 1.50E+05 | 3.38E+02 | 2.65 | 2.65 |
| 9 | B2 | 1.50E+05 | 0.00E+00 | 5.18 | 5.18 |
| 10 | B3 | 1.50E+05 | 0.00E+00 | 5.18 | 5.18 |
| 11 | B4 | 1.50E+05 | 0.00E+00 | 5.18 | 5.18 |
| 12 | 1B5 | 1.50E+05 | 2.50E+00 | 4.78 | 4.78 |
| 13 | C1 | 1.50E+05 | 6.00E+01 | 3.40 | 3.40 |
| 14 | C2 | 1.50E+05 | 5.00E+00 | 4.48 | 4.48 |
| 15 | C3 | 1.50E+05 | 7.50E+00 | 4.30 | 4.30 |
| 16 | C4 | 1.50E+05 | 0.00E+00 | 5.18 | 5.18 |
| 17 | D1 | 1.50E+05 | 2.75E+01 | 3.74 | 3.74 |
| 18 | D2 | 1.50E+05 | 0.00E+00 | 5.18 | 5.18 |
| 19 | D3 | 1.50E+05 | 0.00E+00 | 5.18 | 5.18 |
| 20 | E1 | 1.50E+05 | 1.25E+01 | 4.10 | 4.10 |
| 21 | E2 | 1.50E+05 | 4.00E+01 | 3.57 | 3.57 |
| NC | None | 1.50E+05 | 1.89E+05 | 0.00 | 0.00 |
| PC | None | 1.50E+05 | 7.50E+00 | 4.30 | 4.40 |
| IC | None | 1.50E+05 | 1.90E+05 | −0.10 | −0.10 |
| UC | None | 0.00E+00 | 0.00E+00 | NA | NA |

*K. pneumoniae*
1.50E+05 = 150,000 cfu/ml.

Spunlaced fabric of poly(metaphenylene isophthalamide) fibers (1.5 dpf) sold commercially as "Sontara" style E-88 by E. I. du Pont de Nemours and Company were irradiated in the following examples. The fabric had a basis weight of 31 g/m² and a specific surface area of 0.234 m²/g.

Poly(metaphenylene isophthalamide) spunlaced fabric was irradiated at an energy of 10.9 J/cm² as detailed in the Radiation Conditions described in Table I. These examples did not evidence significant antimicrobial activity in 1 hour exposure to initial Klebsiella populations of 1.05E+03 to 1.05E+05 cfu/ml. After 24 hour exposure to irradiated samples, antimicrobial activity was evidenced in most examples as shown in Table III.

TABLE III

Antimicrobial Activity Associated with Poly(metaphenylene isophthalamide) Spunlaced Fabric Irradiated with 10.9 J/cm²

| Example | Radiation Treatment | Initial* cfu/ml | 1 Hour cfu/ml | $k_t$ | $D_t$ |
|---|---|---|---|---|---|
| IC | None | 1.05E+04 | 5.98E+03 | 0.25 | −0.41 |
| IC | None | 1.05E+05 | 6.45E+04 | 0.36 | −0.46 |
| UC | None | 0.00E+00 | 0.00E+00 | NA | NA |
| 22 | A6 | 1.05E+03 | 0.00E+00 | 3.02 | 1.70 |
| 23 | B5 | 1.05E+03 | 5.00E+00 | 2.24 | 0.92 |
| 24 | C4 | 1.05E+03 | 2.35E+02 | 0.67 | −0.65 |
| 25 | D3 | 1.05E+03 | 1.09E+03 | 0.20 | 1.12 |
| 26 | E2 | 1.05E+03 | 3.00E+03 | −0.46 | −1.78 |
| 27 | A6 | 1.05E+04 | 5.00E+01 | 2.45 | 1.79 |
| 28 | B5 | 1.05E+04 | 2.50E+00 | 3.63 | 2.97 |
| 29 | C4 | 1.05E+04 | 1.46E+03 | 1.52 | 0.86 |
| 30 | D3 | 1.05E+04 | 2.25E+04 | −0.32 | −0.99 |
| 31 | E2 | 1.05E+04 | 3.00E+04 | −0.46 | −1.12 |
| 32 | A6 | 1.05E+05 | 2.50E+00 | 4.63 | 3.81 |
| 33 | B5 | 1.05E+05 | 2.50E+00 | 4.63 | 3.81 |
| 34 | C4 | 1.05E+05 | 2.38E+03 | 1.88 | 1.06 |
| 35 | D3 | 1.05E+05 | 5.27E+04 | 0.52 | −0.31 |
| 36 | E2 | 1.05E+05 | 3.00E+05 | −0.46 | −1.28 |
| 37 | None | 1.05E+03 | 5.00E+00 | 1.32 | −0.01 |
| 38 | None | 1.05E+04 | 2.27E+03 | 0.83 | 0.16 |
| 39 | None | 1.05E+05 | 1.58E+04 | 0.85 | 0.03 |
| NC | None | 1.05E+03 | 1.28E+02 | 2.87 | 0.08 |
| PC | None | 1.05E+03 | 0.00E+00 | 4.90 | 2.11 |

*K. pneumoniae*

YARN EXAMPLES

Poly(hexamethylene adipamide) yarn (sold commercially by E. I. du Pont de Nemours and Company and designated 200-34-R35 Type 496 nylon yarn) having a denier per filament of 5.9 and a specific surface area of 0.130 m²/g was irradiated in accordance with the process of the invention. The yarn was drawn about 3.5× in the course of its manufacture. Results are detailed in Table IV.

To irradiate the yarn, the untwisted yarn was spread so that most of its surface area was irradiated as determined by scanning electron microscope. The 34-filament yarn was spread into a double layer of filaments by first passing the yarn through a standard three roll tensioning device, adding enough tension (40 to 50 g), and then wrapping it 4.5 turns around a pair of air-bearing rolls, slightly canted to advance the yarn. Each wrap was advanced about 1 mm from the preceding wrap with 5 turns on the laser side and 4 behind. Thus, the yarn, spread into a ribbon, was passed at 1.10 meters per second directly in front of the laser beam positioned between the pair of air bearing rolls. All 4.5 wraps were in the 1.76 cm² beam area. The beam impinged directly on one side of the ribbon during the 5 turns on the laser side and on the opposite side of the ribbon during the 4 turns on the back side. A 193 nm mirror was mounted behind the yarn in the laser beam path to reflect the energy back to the spread yarn. Under these conditions, approximately 50% of the energy was returned from the mirror. The yarn was wound on a bobbin after being irradiated. After a pass, the ribbon was collapsed by unwinding under low tension using a rolling take off and was reformed with a different array on each succeeding pass. The procedure was repeated for a total of 20 passes.

An Excimer laser model EMG 202MSC was operated without a lens at 100 Hz, 150 mJ/pulse and at an average power of 15W so that the energy per pass was 0.6 J/cm². The irradiance was about 5.3 MW/cm². It is inherent in multiple pass processes that some areas receive greater energy than others, so the total energy represents an average. It can be noted that for each pass, about 50% of the specific surface area of the yarn was exposed to both the direct and reflected laser radiation. After 5 passes, specific surface area exposure increased to nearly 100%.

Antimicrobial activity of the yarn as determined by the Shake Flask Test demonstrates a greater than 4 log kill in one hour as shown in Table IV.

TABLE IV

Antimicrobial Activity Associated with Poly(hexamethylene adipamide) Yarn Irradiated with 12 J/cm$^2$ Energy

| Example | Radiation Treatment | 1 Hour cfu/ml | $k_t$ | $D_t$ |
|---|---|---|---|---|
| IC | None | 3.31E+04 | 0.01 | 0.16 |
| NC | None | 2.03E+04 | 0.23 | 0.00 |
| PC | None | 0.00E+00 | 4.53 | 4.31 |
| 40 | None | 4.68E+04 | −0.14 | 0.01 |
| 41 | None | 4.95E+04 | −0.16 | −0.01 |
| 42 | 12 J/cm$^2$ | 0.00E+00 | 4.53 | 4.68 |
| 43 | 12 J/cm$^2$ | 0.00E+00 | 4.53 | 4.68 |

Initial concentration *K. pneumoniae* = 3.41E+04 cfu/ml

Undrawn poly(hexamethylene adipamide) yarn was prepared by spinning flake into a 51 filament yarn having a total bundle denier of 200. The yarn had a specific surface area of 0.159 m$^2$/g, a relative viscosity of 48.5 and 44 equivalents of amine ends per 10$^6$ g.

The yarn was wound on the drum roller used in the spunlaced fabric examples described above. Prior to winding the yarn on the drum, a strip of tape was placed axially on the drum. The yarn was irradiated on the drum with an Excimer laser LPX 325iCC operating without a lens at 250 Hz and 200 mJ/pulse. The drum was rotated at 30.3 RPM and with a lateral speed of 0.0254 m/min. This resulted in each unit area of the yarn being irradiated with 180 pulses of 67 mJ/cm$^2$ each for a total energy of 12.0 J/cm$^2$. The irradiance was about 4.2 MW/cm$^2$. After one side had been irradiated, a second strip of tape was placed on it in the same location as the first strip of tape. The yarn was then cut off the drum by slitting along the middle of the taped portion. The warp was then turned over, placed back on the drum and irradiated on the other side. The fraction of surface area irradiated could not be ascertained directly since fibers having very low orientation do not develop the characteristic surface structures during irradiation. However by analogy with Examples 46 and 47, greater than half of the specific surface area was irradiated. After one hour exposure to the material as seen in Example 45, Table V, the bacterial population was reduced below the limit of detection.

TABLE V

Antimicrobial Activity Associated with Undrawn Poly(hexamethylene adipamide) Yarn

| Example | Radiation Treatment | 1 Hour cfu/ml | $k_t$ | $D_t$ |
|---|---|---|---|---|
| 44 | None | 1.85E+04 | 0.28 | 0.00 |
| 45 | 12 j/cm$^2$ | 0.00E+00 | 3.54 | 3.27 |
| IC | None | 1.10E+05 | −0.49 | −0.77 |
| UC | None | 0.00E+00 | NA | NA |

Initial concentration *K. pneumoniae* = 3.5E+04 cfu/ml

Poly(ε-caproamide) yarn (sold commercially by Allied Signal Corp. as 40-12 denier 100% Type-6 nylon yarn was irradiated as described above for Examples 44 and 45 with 12.0 J/cm$^2$. The specific surface area of this 3.3 dpf yarn was 0.173 m$^2$/g. Scanning electron photomicrographs indicated that greater than 50% of the surface area had been irradiated.

TABLE VI

Antimicrobial Activity Associated with Irradiated poly(ε-caproamide) Yarn

| Example | Radiation Treatment | 1 Hour cfu/ml | $k_t$ | $D_t$ |
|---|---|---|---|---|
| 46 | None | 5.2E+04 | 0.22 | 0.00 |
| 47 | 12 J/cm$^2$ | 0.0E+00 | 4.93 | 4.72 |
| IC | None | 8.1E+04 | 0.03 | −0.19 |
| UC | None | 0.0E+00 | NA | NA |

Initial Concentration *K. pneumoniae* = 8.6E+04 cfu/ml

Poly(hexamethylene adipamide) yarn modified with 2.4% by weight of N,N'-bis(3-aminopropyl)piperazine (APP) by stoichiometrically replacing a portion of the hexamethylene diamine monomer with (APP)(sold commercially by E. I. du Pont de Nemours and Company as 100-34-R25 Type 181B deep-dye automotive yarn) was irradiated on the drum winder as described above for Examples 44 and 45 with an energy of 12.0 J/cm$^2$. The drawn yarn has a relative viscosity of 40 and 112 total titratable amine ends per 10$^6$ g. This yarn has a specific surface area of 0.184 m$^2$/g. Greater than 50% of the specific surface area of the yarn was irradiated as determined by scanning electron microscope. Antimicrobial activity is shown in Table VII.

Undrawn Poly(hexamethylene adipamide) yarn modified with 2.4% by weight of N,N'-bis(3-aminopropyl)-piperazine:

The flake used in producing the yarn of Examples 50 and was spun on a small spinning unit into a 200 denier undrawn yarn having 51 filaments. The yarn had a relative viscosity of 31, 130 equivalents of titratable amine ends per 10$^6$ g and a specific surface area of 0.159 m$^2$/g. The yarn was irradiated on the drum winder as described above for Examples 44 and 45 with an energy of 12.0 J/cm$^2$. Greater than 50% of the specific surface area of the yarn was irradiated by analogy with Examples and 51. Antimicrobial activity is shown in Table VII.

TABLE VII

Antimicrobial Activity Associated with Irradiated Poly(hexamethylene adipamide) modified with 2.4% by weight of N,N'-bis(3-aminopropyl)-piperazine

| Example | Material | Radiation Treatment | 1 Hour cfu/ml | $k_t$ | DT |
|---|---|---|---|---|---|
| 48 | Undrawn | 12 J/cm$^2$ | 2.5E+00 | 4.44 | 4.09 |
| 49 | Undrawn | None | 3.1E+04 | 0.35 | 0.00 |
| 50 | Drawn | 12 J/cm$^2$ | 0.0E+00 | 4.84 | 4.78 |
| 51 | Drawn | None | 6.0E+04 | 0.06 | 0.00 |
| IC | — | None | 7.4E+04 | −0.03 | −0.21 |
| UC | — | None | 0.0E+00 | NA | NA |

Initial concentration *K. pneumoniae* = 6.9E+04 cfu/ml

KNIT AND WOVEN FABRIC EXAMPLES

Knit fabric of poly(hexamethylene adipamide) monofilament sold commercially as 15-1 denier type 280 nylon 66 by E. I. du Pont de Nemours and Company was irradiated. The tricot knit fabric had the following characteristics:
Specific surface area =0.08 m$^2$/g
Wales=46 ends
Courses=43 ends
Thickness=0.007 BSI British standard units Specific volume (bulk)=5.41
Fabric weight=0.97 oz/yd$^2$ The fabric was placed on the drumroller used for the spunlaced fabric examples. The drum roller rotated at 30 rpm with a lateral speed of 0.45 m/min. An Excimer laser model LPX 325iCC was operated at 250 Hz and 200 mJ/pulse resulting in each area receiving 10 pulses or 0.67 J/cm$^2$/pass. The irradiance was about 4.2 MW/cm$^2$. Greater than 40% of the surface area of the fabric was irradiated. Results are shown in Table VIII.

Plain Woven fabric of poly(hexamethylene adipamide) of 40-34 denier fiber sold commercially as Type 285 SD nylon 66 by E. I. du Pont de Nemours and Company were irradiated. The woven fabric had the following characteristics:

Specific surface area=0.290 m$^2$/g
Warp=178 ends/inch
Thickness=0.004 inches (ASTM)
Weight=1.61 oz/yd$^2$
Specific volume (bulk)=1.86
Fill=112 ends/inch The fabric was irradiated as described for the knit fabric Examples 58 to 63. Less than 6% (less than 0.02 m$^2$/g) of the surface area of the fabric was irradiated.

Spunlaced fabric of poly(hexamethylene adipamide) prepared as described for Examples 1 to 21 (Table X), spores of *Bacillus circulans* (Table XI) and Bacteriophage T4 (Table XII), *Staphylococcus aureus* (Example 74) and *Escherichia coli* (Example 75).

For Examples 66 to 75, irradiated poly(hexamethylene adipamide) spunlaced fabric and yarn were employed in the Shake Flask Test. The spunlaced fabric used as controls in the Shake Flask Test of Examples 66, 68, 70 and 72 was the same type of spunlaced fabric described above and employed in Example 1. The spunlaced fabric in the Shake Flask Test of Examples 67, 69, 71, 73, 74 and 75 was irradiated as described for Examples 1 to 21, except that an Excimer laser model LPX 325iCC was operated without a lens at 250 Hz and 200mJ/pulse and each side was exposed to 4 to 6 passes of the laser for a total energy as indicated. The irradiance was about 4.2 MW/cm$^2$. The drum was operated at 30 rpm and the lateral speed of the drum was 17.7 inches/minute. The yarn used in the Shake Flask Test of Example 73 was irradiated as described above for Examples 42 and 43. The yarn used in Example 74 was the same yarn employed in Examples 40 and 41.

TABLE VIII

Antimicrobial Activity Associated with Laser Irradiated Knit and Woven fabrics of poly(hexamethylene adipamide)

| Example | Material Type | Passes Per Side | J/cm$^2$ per side | 1 Hour cfu/ml | k$_t$ | Δ$_t$ | 24 Hour cfu/ml | k$_t$ | Δ$_t$ |
|---|---|---|---|---|---|---|---|---|---|
| 52 | Woven | 0 | 0.00 | 6.5E+04 | 0.00 | 0.00 | 2.05E+05 | −0.50 | 0.00 |
| 53 | Woven | 1 | 0.64 | 4.8E+04 | 0.13 | 0.13 | 1.04E+05 | −0.20 | 0.29 |
| 54 | Woven | 2 | 1.32 | 4.6E+04 | 0.15 | 0.15 | 8.15E+04 | −0.10 | 0.40 |
| 55 | Woven | 4 | 2.64 | 5.4E+04 | 0.08 | 0.08 | 2.30E+05 | −0.55 | −0.05 |
| 56 | Woven | 8 | 5.28 | 5.9E+04 | 0.04 | 0.04 | 1.45E+05 | −0.35 | 0.15 |
| 57 | Woven | 16 | 10.56 | 2.5E+04 | 0.41 | 0.41 | 3.10E+02 | 2.32 | 2.82 |
| 58 | Knit | 0 | 0.00 | 5.7E+04 | 0.06 | 0.00 | 1.95E+05 | −0.48 | 0.00 |
| 59 | Knit | 1 | 0.66 | 9.5E+01 | 2.82 | 2.76 | 0.00E+00 | 4.11 | 4.59 |
| 60 | Knit | 2 | 1.32 | 2.5E+00 | 4.41 | 4.36 | 0.00E+00 | 4.81 | 5.29 |
| 61 | Knit | 4 | 2.64 | 5.0E+00 | 4.11 | 4.06 | 0.009+00 | 4.81 | 5.29 |
| 62 | Knit | 8 | 5.20 | 1.0E+01 | 3.81 | 3.76 | 0.00E+00 | 4.81 | 5.29 |
| 63 | Knit | 16 | 10.56 | 0.0E+00 | 4.81 | 4.76 | 0.00E+00 | 4.81 | 5.29 |
| 64 | Spunlaced | 0 | 0.00 | 5.9E+04 | 0.04 | 0.00 | 8.959+05 | −1.14 | 0.00 |
| 65 | Spunlaced | 4 | 10.64 | 7.5E+00 | 3.94 | 3.90 | 0.00E+00 | 4.01 | 5.93 |
| IC | | NA | NA | 6.5E+04 | 0.00 | −0.03 | 1.05E+05 | −0.21 | −0.24 |
| UC | | NA | NA | 0.0E+00 | NA | NA | 0.00E+00 | NA | NA |

Initial Concentration = 6.5E+04 cfu/ml, *K. pneumoniae* was used as a control for Example 64. The irradiated spunlaced fabric of Example 65 was irradiated according to Radiation Treatment A4 as set forth in Table I.

As shown in Table VIII, after 24 hours exposure to irradiated woven fabric antimicrobial activity was evident only in Example 57 which was exposed to a very high level of radiation.

After 1 hour exposure to irradiated knit fabric, the population of *K. pneumoniae* was reduced by greater than 99%. Complete reduction was evident in knit fabric Examples 59 to 63 by 24 hours.

BROAD SPECTRUM ACTIVITY EXAMPLES

To illustrate the broad spectrum activity of the material produced by the process of this invention, the Shake Flask Test as described herein was conducted replacing *K. pneumoniae* with a variety of other microorganisms.

Antimicrobial activity associated with laser irradiated poly(hexamethylene adipamide) materials produced by the process of the invention have a broad activity as evidenced by the ability to reduce populations of *Aspergillus niger* (Table IX), *Candida albicans*

TABLE IX

Activity of Irradiated Spunlaced Fabric of Poly(hexamethylene adipamide) to *Aspergillis niger*.

| Example | Radiation Treatment | 1 Hour pg/ml | k$_t$ | D$_t$ |
|---|---|---|---|---|
| 66 | None | 4.3E+04 | 0.37 | 0.00 |
| 67 | 3.33 J/cm$^2$/side | 2.2E+02 | 2.66 | 2.29 |
| IC | None | 1.4E+05 | −0.15 | −0.51 |
| UC | None | 0.0E+00 | NA | NA |

Initial Concentration *A. niger* = 1.0E+05 propagules/ml (pg/ml)

TABLE X

Activity of Irradiated Spunlaced Fabric of Poly(hexamethylene adipamide)

| Example | Radiation Treatment | 1 Hour pg/ml | k$_t$ | D$_t$ |
|---|---|---|---|---|
| 68 | None | 9.8E+04 | −0.19 | 0.00 |
| 69 | 4.0 J/cm$^2$/side | 1.0E+02 | 2.80 | 2.99 |
| IC | None | 1.2E+05 | −0.28 | −0.09 |
| UC | None | 0.0E+O | NA | NA |

Initial concentration *C. albicans* = 6.3E+04 cfu/ml

TABLE XI

Activity of Irradiated Spunlaced Fabric of Poly(hexamethylene adipamide) to *Bacillus circulans* spores.

| Example | Radiation Treatment | 1 Hour cfu/ml | $k_t$ | $D_t$ |
|---|---|---|---|---|
| 70 | None | 1.5E+03 | 0.27 | 0.00 |
| 71 | 2.66 J/cm²/side | 2.0E+01 | 2.14 | 1.88 |
| IC | None | 2.5E+03 | 0.04 | −0.22 |
| UC | None | 0.0E+0 | NA | NA |

Initial Concentration *B. circulans* = 2.8E+03 cfu/ml

TABLE XII

Activity of Irradiated Yarn of Poly(hexamethylene adipamide) to Bacteriophage T4.

| Example | Radiation Treatment | 1 Hour pg/ml | $k_t$ | $D_t$ |
|---|---|---|---|---|
| 72 | None | 2.48E+05 | −0.16 | 0.00 |
| 73 | 12 J/cm² | 0.00E+00 | 5.23 | 5.39 |
| IC | None | 2.96E+05 | −0.24 | −0.07 |

Initial Concentration Bacteriophage T4 = 1.7E+05 plaque forming units (pfu/ml).

EXAMPLES 74 and 75

Comparable antimicrobial activity against *Staphylococcus aureus* and *Escherichia coli* was evident in experiments similar to those described for *A. niger* as detailed in Table IX. Within 24 hours, a *S. aureus* population was reduced from 7.51E+03 cfu/ml to <10 cfu/ml, i.e. a greater than 3.9 log kill. A population of *E. coli* was similarly reduced from 1.05E+05 cfu/ml to <10 cfu/ml, i.e. a greater than 5 log kill.

COMPOSITIONS CONTAINING SUBSTITUTED UREA GROUPS

EXAMPLE 76

Urea-formaldehyde resin solution (available from Cargill, Inc. Minneapolis, Minn. 55440) was dried by evaporating the solvent, suspended, and then stirred in deionized water for 24 hours. Ten grams (10) of solids (powder) were separated from the liquid by filtration and dried in air at ~35° C.

The mass of polymer was then divided into two, five-gram batches. One batch was reserved as a control (Sample 10987-49-6 in Table XIII). The other batch was irradiated according to the following procedure.

Five grams of polymer powder were placed into a 250 ml beaker. The beaker was secured to a ring stand at its top, and the beaker was mounted on a test-tube vortexing device in order to rapidly vibrate the vessel in a circular motion about its vertical axis. In so doing, the powder contained in the beaker underwent rapid convection thus continually renewing the powder surface.

The top of the flowing powder bed was then irradiated in air using a Lambda-Physik, Excimer Laser, Model LPX 325iCC which emitted photons having a wavelength of 193 nm. The laser power delivered to the powder mass equaled 20 watts for a period of 10 minutes. The laser energy was delivered in a pulsed fashion, each pulse lasting 16 nanoseconds, at a rate of 100 hertz.

The laser treated powder is identified as Sample 10987-49-5 in Table XIII.

The two powder samples were then tested for antimicrobial properties using the following procedures. Both the control powder and the irradiated powder were separately suspended in liquid phosphate buffer for twenty-four hours in order to extract any leachable toxins which may have been present. Both powder samples were then filtered from the extraction liquid, suspended in fresh phosphate buffer and then tested for antimicrobial activity against *Klebsiella pneumoniae* using the Shake Flask Test.

The antimicrobial results are shown in Table XIII, below.

TABLE XIII

| control polymer (10987-49-6) | | | | irradiated polymer (10987-49-5) | | | |
|---|---|---|---|---|---|---|---|
| solid | | liquid | | solid | | liquid | |
| kt @1 hour | kt @24 hrs. | kt @1 hour | kt @24 hrs. | kt @1 hour | kt @24 hrs. | kt @1 hour | kt @24 hrs. |
| 0.33 | 0.34 | 0.42 | 0.38 | 1.47 | 5.04 | 0.37 | 0.24 |

HIGH ENERGY ELECTRON BEAM IRRADIATION EXAMPLES

EXAMPLE 77 to 107

The following examples illustrate the preparation of antimicrobial poly(hexamethylene adipamide) articles using a high energy electron beam source.

The irradiated articles were either spunlaced poly(hexamethylene adipamide) fabric: (poly(hexamethylene adipamide) fibers sold commercially by E. I. du Pont de Nemours and Company, as style 200SD having a dpf of 1.8 (0.2 Tex) were spunlaced to yield a fabric), and identified as "S-1" or "S-2" in Table XIV, or poly(hexamethylene adipamide) membrane sold commercially as "Genescreen" by E. I. du Pont de Nemours and Company and identified as "G" in Table XIV.

For all examples shown in Table XIV, the electron beam accelerator, available from High Voltage Inc., Model KS, was operated using the following settings and conditions. The electron beam accelerator had an output of 3 MeV electrons with a total beam current of 0.6 amp. The width of the beam was 15 inches, and the distance of the beam to the sample window was set at 6 inches. The conveyor belt speed was 93 inches/minute. The samples were placed flat on the conveyer belt and passed under the beam window by mechanical operation of the belt. At each pass through the beam window, the delivered dose was 0.5 MRad. The samples had enough cumulative passes to achieve the desired final dose. For the examples in Table XIV, the fabric or membrane (2.0 g, 20×24 cm²) was sealed inside two thin bags. The inner bag was zip-locked polyethylene, and the outer bag was aluminized "Tyvek". Some spunlaced fabric samples were sealed under a blanket of nitrogen or argon, but most samples were sealed under a normal air atmosphere. For delivered beam dosages which exceeded 20 MRad, typical exponential kill values for *Klebsiella pneumoniae* were 5.00 kt at 24 hr microbe contact time.

TABLE XIV (Antimicrobial Activity Associated with Poly(hexamethylene adipamide) Irradiated with High Energy Electrons)

| Ex. # | Art.[1] Type | Atmos.[2] | Beam Passes | Radiation Delivered | Dose (Mrad)[3] | Initial cfu/mL[4] | kt @24 h |
|---|---|---|---|---|---|---|---|
| 77 | S-1 | Air | 0 | 0 | | 4.00E+04 | −0.65 |
| 78 | S-1 | Air | 0 | 0 | | 1.20E+05 | −0.62 |
| 79 | S-2 | Air | 0 | 0 | | 1.20E+05 | −0.83 |
| 80 | S-1 | Air | 5 | 2.5 | | 1.20E+05 | −0.52 |
| 81 | S-1 | N2 | 5 | 2.5 | | 1.20E+05 | 0.32 |
| 82 | S-2 | Air | 5 | 2.5 | | 1.20E+05 | −0.54 |
| 83 | S-2 | N2 | 5 | 2.5 | | 1.20E+05 | −0.58 |
| 84 | S-1 | Air | 6 | 3.0 | | 9.4E+04 | 2.55 |
| 85 | S-1 | Ar | 6 | 3.0 | | 9.4E+04 | 1.16 |
| 86 | S-1 | Air | 20 | 10 | | 1.20E+05 | 0.32 |
| 87 | S-1 | N2 | 20 | 10 | | 1.20E+05 | 0.47 |
| 88 | S-2 | Air | 20 | 10 | | 1.20E+05 | 0.36 |
| 89 | S-2 | N2 | 20 | 10 | | 1.20E+05 | −0.24 |
| 90 | S-1 | Air | 40 | 20 | | 1.20E+05 | 0.89 |
| 91 | S-1 | N2 | 40 | 20 | | 1.20E+05 | 3.14 |
| 92 | S-2 | Air | 40 | 20 | | 1.20E+05 | 4.30 |
| 93 | S-2 | N2 | 40 | 20 | | 1.20E+05 | 1.25 |
| 94 | S-1 | Air | 60 | 30 | | 1.20E+05 | 5.08 |
| 95 | S-1 | N2 | 60 | 30 | | 1.20E+05 | 5.08 |
| 96 | S-1 | N2 | 60 | 30 | | 1.10E+05 | 5.04 |
| 97 | S-2 | Air | 60 | 30 | | 1.20E+05 | 5.08 |
| 98 | S-2 | N2 | 60 | 30 | | 1.20E+05 | 5.08 |
| 99 | S-1 | N2 | 100 | 50 | | 1.10E+05 | 5.04 |
| 100 | S-1 | N2 | 110 | 55 | | 1.10E+05 | 5.04 |
| 101 | S-1 | Air | 120 | 60 | | 1.20E+05 | 5.08 |
| 102 | S-1 | N2 | 120 | 60 | | 1.20E+05 | 2.20 |
| 103 | S-2 | Air | 120 | 60 | | 1.20E+05 | 4.54 |
| 104 | S-2 | N2 | 120 | 60 | | 1.20E+05 | 5.08 |
| 105 | S-1 | N2 | 170 | 85 | | 1.10E+05 | 5.04 |
| 106 | S-1 | N2 | 180 | 90 | | 1.10E+05 | 5.04 |
| 107 | G | N2 | 60 | 30 | | 1.10E+05 | 4.26 |

NOTES FOR TABLE:
[1]Article Type: S: spunlaced poly(hexamethylene adipamide)
G: "GeneScreen"
-1: washed with "Tide" to remove fabric finishes.
-2: washed with hot water to remove fabric finishes.
[2]Atmosphere: Air; Nitrogen (N2); or Argon (Ar).
[3]1.0 MRad = 10 Joules/g.
[4]*Klebsiella pneumoniae* as the test microbial population

LOW ENERGY ELECTRON BEAR IRRADIATION EXAMPLES

EXAMPLE 108

An approximately 8 inch × 8 inch square of spunlaced poly(hexamethylene adipamide) fabric: (poly(hexamethylene adipamide) fibers sold commercially by E. I. du Pont de Nemours and Company, as style 200SD having a dpf of 1.8 (0.2 Tex) were spunlaced to yield a fabric), and having a basis weight of 0.95 ounce/square yard was cleaned with hot water to which 0.25 g/L of "Merpol HCS" surfactant, sold by E. I. du Pont de Nemours and Company, had been added. The fabric was treated on both sides by the low energy electron beam apparatus in the manner described previously under Testing Conditions. The filament current was set to 0.9 amperes, the beam voltage was maintained at 500 volts, the platen was rotated at 60 rotations per minute, and the treatment continued for 15 seconds. Examination by X-ray Photoelectron Spectroscopy (XPS) of a sample cut from the region that had passed directly over the filament assembly showed a decrease in the fraction of the carbon 1s peak attributable to carbonyl from 13-14% to 10-12%. In the Shake Flask Test for antimicrobial activity, the material taken from the region that passed directly above the filament reduced the *Klebsiella pneumonias* population 2.84 logs in one hour and eliminated the population entirely in 24 hours (a 4.75 log reduction).

EXAMPLE 109

An approximately 8 inch × 8 inch square of spunlaced poly(hexamethylene adipamide) fabric: (poly(hexamethylene adipamide) fibers sold commercially by E. I. du Pont de Nemours and Company, as style 200SD, having a dpf of 1.8 (0.2 Tex) were spunlaced to yield a fabric), and having a basis weight of 0.95 ounce/square yard was cleaned with hot water to which 0.25 g/L of "Merpol HCS" surfactant had been added. The fabric was treated in the same manner as described in Example 108, except that the treatment time was 150 seconds. The ring of material that had passed directly over the filament was light tan instead of the original white. The x-ray photoelectron spectrum of the carbon 1s peak could not be separated into carbonyl and aliphatic components using the parameters applied to material treated for 15 seconds. Accounting for all the spectral intensity required introduction of a third component or changing the parameters for carbonyl components by more than 20%. The surface chemistry of this material is therefore different from that of the other materials. In the Shake Flask Test for antimicrobial activity, a 0.13 log decrease in the Klebsiella pneumoniae population occurred after one hour, and there was a 0.37 log increase after 24 hours.

EXAMPLE 110

An approximately 8 inch×8 inch square of spunlaced poly(hexamethylene adipamide) fabrics: (poly(hexamethylene adipamide) fibers sold commercially by E. I. du Pont de Nemours and Company, as style 200SD having a dpf of 1.8 (0.2 Tex) were spunlaced to yield a fabric) and having a basis weight of 0.95 ounce/square yard was cleaned with hot water to which 0.25 g/L of "Merpol HCS" surfactant had been added. The fabric was treated in the same manner as described in Example 108, except that the treatment time was 2 seconds. X-Ray Photoelectron Spectroscopy (XPS) showed a fraction of the carbon 1s peak attributable to carbonyl of 13%. In the Shake Flask Test for antimicrobial activity, the Klebsiella pneumoniae population was reduced by 2.09 logs in one hour and 3.01 logs after 24 hours.

CHEMICAL REDUCTION EXAMPLES

In the following examples, polyamide fiber was treated with different chemical reagents and subsequently tested for antimicrobial activity. In each of the following examples, the fiber was scoured as follows.

To 1000 ml of deionized water, 0.25 g of the surfactant, "Igepon T-51" available from GAF Corp., was added. The fiber was then added, and the mixture was brought to a slow boil. The mixture was then stirred with a glass rod intermittently for at least 15 min. The fiber was then removed and washed while squeezing, in cold tap water for 5 min and then washed with deionized water for 2 min. The fiber was then air-dried overnight.

EXAMPLE 111

About 200 ml of dry tetrahydrofuran (THF) was added to a dry 500 ml three necked round bottom flask fitted with an overhead stirrer with a glass paddle. After the system was flushed with nitrogen, 1.0 g of lithium aluminum hydride ($LiAlH_4$), available from Aldrich Chemical Co., Milwaukee, Wis. was added gradually and allowed to stir for 45 minutes. When the 45 min was over, 5.0 g of nylon fiber, 6 denier per filament (6 dpf) nylon 66 staple type 110, available from E. I. du Pont de Nemours and Company, that had been scoured and dried overnight in a vacuum oven at 50° C. was added and the paddle was manipulated so that the fiber was completely immersed. Some additional solvent was required to insure complete immersion of the fiber. The reaction was allowed to stir overnight at room temperature under a nitrogen blanket. The reaction was worked up by dropwise sequential addition of excess(~30 ml each) acetone, n-propyl alcohol, water, and a 9:1 mixture of water:formic acid with stirring during the additions. The fiber was then rinsed extensively with water, 10% ammonium hydroxide, and then again with water and dried. The Shake Flask Test results for Klebsiella pneumoniae are given in Table XV.

EXAMPLE 112

About 5.0 g of 1200 denier "Anso IV" 6 nylon BCF, available from Allied Chemical Co., was treated in the same manner as described in Example 111. The Shake Flask Test results for Klebsiella pneumoniae are given in Table XV.

Comparative Example 113

5.0 g of nylon fiber, 6 denier per filament (6 dpf) nylon 66 staple type 110, available from E. I. du Pont de Nemours and Company, were treated in the same manner as described in Example 111, except a 3:1 mixture of diethyl ether:methyl alcohol was used as a solvent and 1.0 g of sodium borohydride was used rather than the lithium aluminum hydride ($LiAlH_4$). The Shake Flask Test results for Klebsiella pneumoniae are given in Table XV.

Comparative Example 114

About 5.0 g of nylon fiber, 6 denier per filament (6 dpf) nylon 66 staple type 110, available from E. I. du Pont de Nemours and Company, were treated with 0.8% sodium borohydride solution and wrung out to 70% liquid absorption. The sodium borohydride was not washed out after the treatment and the strips were dried for 20 minutes at 105° C. The fiber was then rinsed with water. After drying, the strips were heated to 150° C. The Shake Flask Test results for Klebsiella pneumoniae are given in Table XV.

TABLE XV

| | | 1 hr | | 24 hr | |
|---|---|---|---|---|---|
| Example | Sample ID | kt | Dt | kt | Dt |
| 111 | P11037-14 | 2.42 | 2.53 | 4.54 | 4.84 |
| 112 | P11037-14-1 | 4.30 | 4.41 | 5.08 | 5.38 |
| 113 | P11037-15-1 | 0.15 | 0.27 | −0.50 | −0.20 |
| 114 | P11037-17 | 0.03 | 0.14 | 0.32 | 0.62 |
| 115 | Control scoured 66 nylon | −0.11 | 0.00 | 0.30 | 0.00 |

We claim:

1. A process for preparing an inherently antimicrobial, polymeric material, comprising irradiating the surface of a shaped material comprising an organic polymer having carbonyl groups covalently bound to nitrogen in the form of

moieties, said material being in a form having a specific surface area such that at least 0.02 m²/g of the material is irradiated with an ultraviolet photon energy density of at least 300 mJ/cm² at a wavelength of no greater than 222 nm and wherein the absorption coefficient for the material is at least 1,5/D, where D is the thickness of the material, whereby said irradiation converts a sufficient amount of said

moieties on the surface of said material to amine or hydrazine moieties to impart antimicrobial activity substantially to the surface of said material, said polymer being selected from the group consisting of a polyamide, polyurea, polyhydrazide, polyurethane, and copolymers and polymer blends thereof.

2. A process for preparing an inherently antimicrobial, polymeric material as defined in claim 1, wherein the source of ultraviolet photons is a laser.

3. A process for preparing an inherently antimicrobial, polymeric material as defined in claim 1, wherein the source of ultraviolet photons is an ultraviolet lamp.

4. The process of claim 1, wherein the polymer is a polyamide.

5. A process for preparing an inherently antimicrobial, polymeric material, comprising irradiating the surface of a shaped material comprising an organic polymer having carbonyl groups covalently bound to nitrogen in the form of

moieties, said material being in a form having a specific surface area such that at least 0.02 m2/g of the material is irradiated with electrons having a kinetic energy of about 6 eV, to 10,000,000 eV at an energy absorption from the electrons of about 10,000 erg/cm³ to 1,000,000 erg/cm³, whereby said irradiation converts a sufficient amount of said

moieties to amine or hydrazine moieties to impart antimicrobial activity to the surface of said material, said polymer being selected from the group consisting of a polyamide, polyurea, polyhydrazide, polyurethane, and copolymers and polymer blends thereof.

6. The process of claim 5, wherein the surface of the shaped material is irradiated with electrons having a kinetic energy of 100 to 5000 eV, at an energy absorption from the electrons of 50,000 to 250,000 erg/cm³ of irradiated volume.

* * * * *